United States Patent [19]

Kirmaier

[11] 4,140,106
[45] Feb. 20, 1979

[54] DRUNKOMETER

[75] Inventor: Norbert Kirmaier, Aschheim near Munich, Fed. Rep. of Germany

[73] Assignee: Sachs-Systemtechnik GmbH, Schweinfurt am Main, Fed. Rep. of Germany

[21] Appl. No.: 754,569

[22] Filed: Dec. 27, 1976

[30] Foreign Application Priority Data

Nov. 30, 1976 [DE] Fed. Rep. of Germany ....... 2654248

[51] Int. Cl.² ............................................. A61B 5/00
[52] U.S. Cl. ................................. 128/2 C; 73/27 R; 73/198
[58] Field of Search ................. 128/2 C, 2.07, 2.08; 23/232 E, DIG. 8; 180/99; 73/27 R, 421.5 R, 231 R, 194, 198; 340/279, 237 R

[56] References Cited

U.S. PATENT DOCUMENTS

| 3,250,270 | 5/1966 | Bloom | 128/2.07 |
|---|---|---|---|
| 3,605,729 | 9/1971 | Liu et al. | 128/2.08 |
| 3,680,378 | 8/1972 | Aurilio et al. | 73/231 R |
| 3,690,838 | 10/1970 | Luckey | 128/2 C |
| 3,695,848 | 10/1972 | Toguchi | 73/27 R |
| 3,764,270 | 10/1973 | Collier et al. | 128/2 C |
| 3,818,901 | 6/1974 | Sancturay et al. | 73/421.5 R X |
| 3,831,707 | 8/1974 | Takeuchi | 128/2 C X |
| 3,842,345 | 10/1974 | Padgitt et al. | 23/232 E X |
| 3,877,291 | 4/1975 | Hoppesch et al. | 73/27 R |
| 3,922,525 | 11/1975 | Kozak et al. | 128/2.08 X |
| 4,036,217 | 7/1977 | Ito et al. | 128/2.08 |
| 4,039,852 | 8/1977 | Miyamoto et al. | 128/2 C X |

FOREIGN PATENT DOCUMENTS 1856621 12/1974 U.S.S.R. .................................. 128/2.08

Primary Examiner—Robert W. Michell
Assistant Examiner—Francis J. Jaworski
Attorney, Agent, or Firm—Hans Berman

[57] ABSTRACT

A drunkometer in which the rate of airflow toward an alcohol vapor sensing device in an input channel is sensed mechanically or electrically, and a resulting flow signal is integrated. The direction of airflow in the input channel is also sensed either by photoelectric means or by a negative-temperature-coefficient resistance and an error signal is furnished if the direction of flow corresponds to inhaled breath. A validity signal signifying that the measured value is a value representative of the concentration of alcohol in the bloodstream is furnished if the integrated signal representing the total exhaled air volume exceeds a predetermined minimum value before an error signal is furnished.

21 Claims, 12 Drawing Figures

DRUNKOMETER

BACKGROUND OF THE INVENTION

This invention relates to apparatus for measuring the alcohol concentration in the breath exhaled by a subject.

It is known that the alcohol concentration in the exhaled air is uniquely related to the alcohol concentration in the blood if the exhaled breath comes from the lungs. Therefore, the subject must exhale a volume of air at least equal to the volume of the mouth cavity and the windpipe before a valid measurement can be obtained. In known equipment, a rate sensor is positioned in the input channel receiving the exhaled breath and the rate sensed must exceed a certain minimum rate for a predetermined period before the value of alcohol concentration as furnished by a gas detector is considered a valid measurement. This arrangement has the disadvantage that the minimum rate must always be exceeded, even so for persons whose normal rate of exhalation is very low and from whose lungs a sample of air could be obtained at a slower rate.

SUMMARY OF THE INVENTION

It is an object of the present invention to furnish apparatus for reliably measuring the alcohol concentration of the blood without requiring the subject whose breath is being measured to exhale at a rate exceeding a predetermined minimum rate.

The present invention provides apparatus for measuring the alcohol content in the breath of a tested subject. It comprises an input arrangement for receiving breath exhaled by the subject. It further comprises an alcohol measuring device in the input for furnishing a signal corresponding to the alcohol content of the breath. Further, a volume measuring device is positioned in the input for furnishing a volume signal when the total volume of air exhaled by the subject exceeds a predetermined minimum. Further positioned in the input is a direction sensing device for sensing the direction of airflow in the input and for furnishing an error signal when the sensed direction is indicative of air being inhaled by the subject. Yet another device furnishes a validity signal indicative of the correspondence of the measurement signal to the actual alcohol content in the bloodstream of the subject only if the volume signal is received prior to the error signal.

Since the ratio between the alcohol concentration in the breath of an individual and that in the blood is approximately 1:2100, small errors in the measured alcohol concentration in the exhaled breath can lead to considerably larger errors in blood concentration. The accuracy of the measurement can be increased substantially if the alcohol in the exhaled air is kept from condensing. The semiconductor gas detector which is used herein in conjunction with a suitable indicator is maintained at a temperature slightly above that of the exhaled air, between 35° and 40° C., to prevent condensation.

Other features, additional objects, and many of the attendant advantages of this invention will readily be appreciated as the same becomes better understood by reference to the following detailed description of preferred embodiments when considered in connection with the appended drawing.

DESCRIPTION OF THE PREFERRED EMBODIMENT

Figure 1:
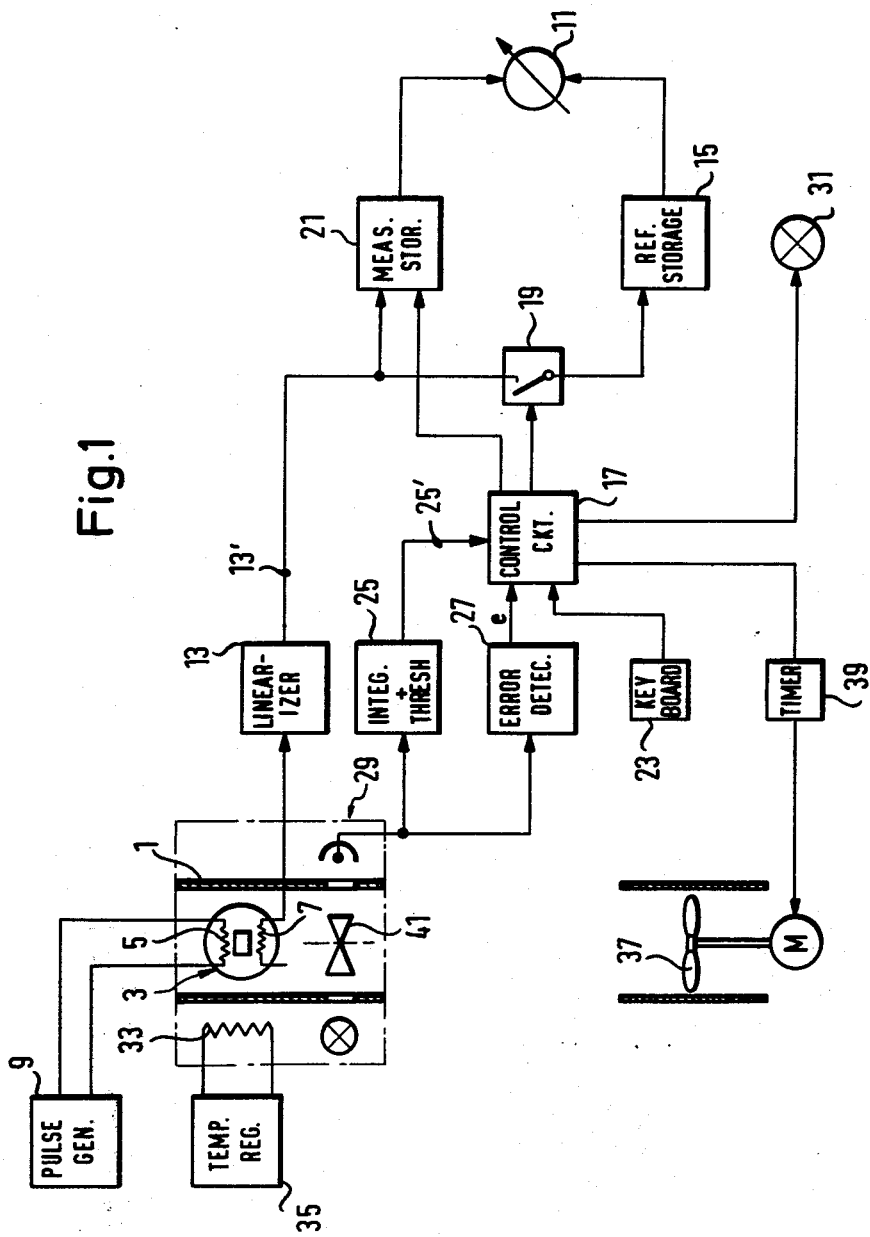
FIG. 1 is a block diagram of a first preferred embodiment of the present invention.

In FIG. 1, an input channel 1 receives the exhaled air. A semiconductor gas detector 3 positioned in channel 1 is a small body having the approximate shape of a parallelepiped and consists of sintered tin oxide, zinc oxide and ferric oxide particles, as is known in itself. Two coil-shaped electrodes 5, 7 are embedded in the semiconductor which absorbs alcohol vapor from an ambient atmosphere to an equilibrium value which, at a given temperature, is a unique function of the alcohol concentration in the atmosphere. The resistance of the semiconductor decreases with the amount of alcohol absorbed. The rate of absorption and desorption also increases with increasing temperature. The spiral ends of electrodes 5, 7 project from the body 3 so that the electrodes may be used as heater filaments. Heating increases both the response time and the recovery time of the unit. In FIG. 1, electrode 5 is connected to a pulse generator 9 which supplies DC pulses of an amplitude substantially higher than would be allowable for continuous DC heating. This type of heating has been found to decrease the response time and the recovery time considerably. However, the average power supplied does not exceed the allowable filament power.

The pulse generator 9 creates a DC potential at electrode 5. The resistance between electrodes 5, 7 varies as an inverse function of the alcohol concentration, and an inversely proportional variation of current between the electrodes results from changes in absorbed alcohol. The amplitude of this current is indicated in indicator 11 which can be calibrated directly in units of alcohol concentration. Since the gas detector tends to saturate at high concentrations, the current is first put through a linearization circuit 13, which linearizes the transfer function of output current versus alcohol concentration. The preferred linearization circuit is an amplifier having an exponentially varying gain.

If measurements follow one another in rapid sequence, desorption after each measurement may be insufficient. Therefore, the signal derived from the linearization circuit 13 is stored in a reference storage 15 prior to the start of a measurement. This is accomplished by briefly closing a switch 19 which causes current to flow from the output of linearization circuit 13 to the input of reference storage 15. Linearization circuit 13 is also connected to a measurement storage 21 which receives the measurement signal under control of a control circuit 17. The measurement signal and the reference signal are applied to opposite terminals of indicating instrument 11. The indication on the indicating instrument is thus a function of the difference between the values stored in storages 21 and 15 which are analog storages, for example of the capacitive type. They are discharged before the start of a measurement by activation of a key in a keyboard 23 which causes a monostable multivibrator in control circuit 17 to be switched to the unstable state. While it is in the unstable state, a base voltage is applied to two transistors, one in parallel with each of the capacitive elements in storages 15 and 21. When this multivibrator (not shown) switches back to the stable state, a second multivibrator (also not shown) is switched to the unstable state causing voltage to be applied to switch 19 which causes the reclosure of the switch. The actual measurement can begin when the second monostable multivibrator switches back to its stable state.

Measurement storage 21 is not enabled until a validity signal is applied thereto by control circuit 17. The validity signal is furnished when a set minimum volume of air has been exhaled by the subject being tested. A rate flow sensor 29 furnishes an output signal, hereinafter referred to as the rate signal, which is proportional to the rate of airflow in channel 1. The rate signal is applied to an integrator and threshold stage 25 where it is continuously integrated with respect to time so that the output of the integrator circuit is a signal indicative of the total volume of air exhaled by the subject from the beginning of the test. When the integrator output signal exceeds a value indicative of the minimum volume of air required for a valid measurement, the threshold stage changes state and a signal, herein referred to as the volume signal, is applied to control circuit 17 through conductor 251.

For a valid measurement, it is also necessary to prevent the tested subject from controlling his breathing in such a way that the air entering channel 1 is not a deep breath sample. Therefore, the signal from sensor 29 is also used to detect the direction of airflow. Error detector 27 to which the signals from sensor 29 are also applied furnishes a signal e to control circuit 17 which prevents release of a validity signal if the subject being tested breathes in before exhaling the minimum volume required for a valid test. The error signal furnished by error detector 27 may also be displayed by an indicator 31. Of course, it is also possible to use indicator 31 to indicate the error without preventing the measured value from being stored and indicated.

To prevent the condensation of alcohol vapor in the exhaled air, an electrical heater 33 maintains in the channel 1 a temperature of approximately 37° C. controlled by a temperature regulating circuit 35. A motor-driven fan 37 directed toward the channel 1 is activated by a key of the keyboard 23 for a time interval determined by a timer 39.

Figure 2:
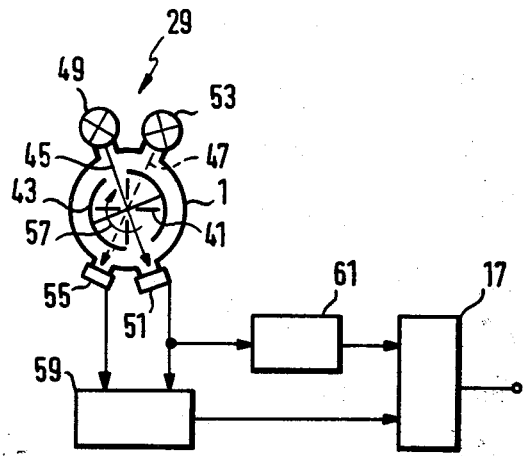
FIG. 2 shows volume measuring and direction sensing devices in the apparatus of FIG. 1 in greater detail.
Figure 2A:
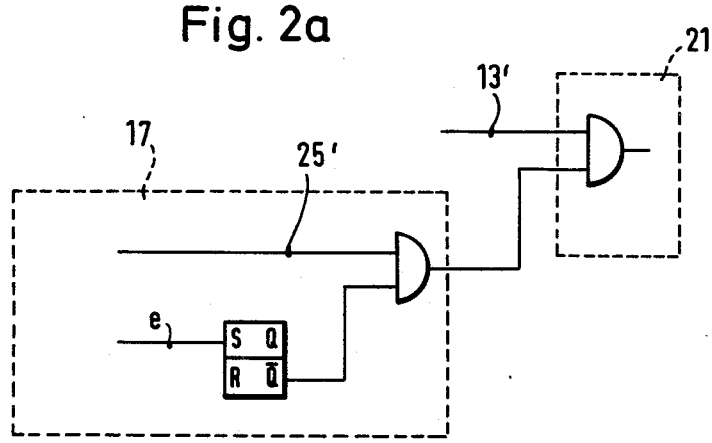
FIGS. 2a and 2b respectively illustrate details of the device of FIG. 2.
Figure 2B:
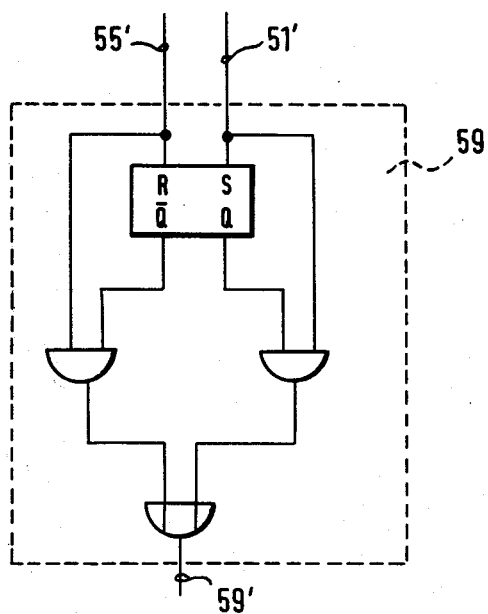

The volume measuring and direction sensing devices represented in FIG. 1 by the sensor 29 and error detector 27 are shown in greater detail in FIG. 2. A turbine 41 (also shown in FIG. 1) is arranged in channel 1 and is rotated by the air flow as indicated by arrow 57. Coupled to turbine 41 and rotatable therewith is a cylindrical diaphragm 43 which periodically interrupts a light beam 45 from a light source 49 to a photoelectric receiver 51 and a light beam 47 from a light source 53 to a photoelectric receiver 55. When turbine 41 is rotated by exhaled air, the light beam 45 causes a signal to be furnished by photoeelectric receiver 51 prior to that furnished by photoelectric receiver 55. The sequence of signals received from the two photoelectric receivers thus corresponds to the direction of rotation of the turbine. A known comparator 59 which evaluates the signals from photoelectric receivers 51 and 55 and is shown in FIG. 2b includes a flip-flop which is set by pulses received from photoelectric receiver 51 through conductor 51' and reset by pulses received from photoelectric receiver 55 through conductor 55'. The Q output of the flip-flop and the signal from photoelectric receiver 51 are applied to the inputs of a first AND gate, while the signals from photoelectric receiver 55 and the Q output of the flip-flop are applied to the inputs of a second AND gate. The outputs of both AND gates are applied to the inputs of an OR gate whose output furnishes the error signal to the comparator 59 through conductor 59'. The operation of this circuit is based on the fact that the flip-flop should not be in the SET state when signals are received from photoelectric receiver 51, nor in the reset state when signals are received from photoelectric receiver 55. The circuit provides a slight delay following the receipt of the pulses from the photoelectric receivers and prior to the actual switching of the flip-flop.

The integrator and threshold stage 25 shown in FIG. 1 are embodied in a counter 61. The counter is preset to a number representing the predetermined minimum air volume by control circuit 17, and the pulses from photoelectric receiver 51 are utilized for a count-down. A count of zero causes a signal, the volume signal, to be applied to control circuit 17. Control circuit 17 furnishes the validity signal if the volume signal is received prior to receipt of an error signal. In a preferred embodiment of the invention, the error signal e sets a flip-flop in control circuit 17, as is shown in FIG. 2a. The Q output of the flip-flop, that is the signal indicating the absence of an error signal, is applied to one input of an AND gate whose second input receives the volume signal through conductor 25'. The output of the AND gate is the validity signal, namely a signal which appears only if the volume signal is received while the Q output of the flip-flop set by the error signal is still high, that is before receipt of the error signal.

Figure 3:
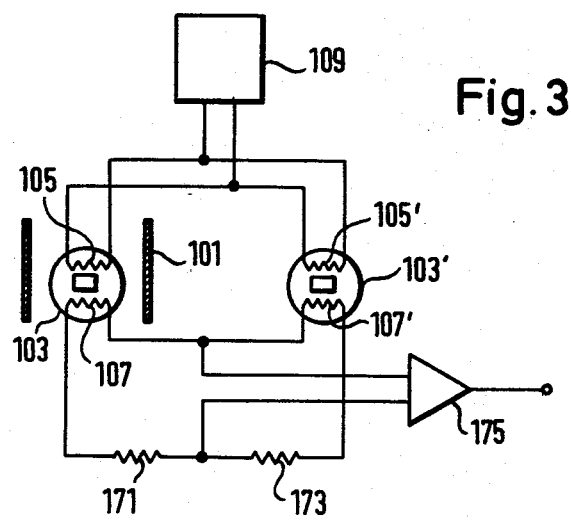
FIG. 3 illustrates a bridge circuit arrangement which can be substituted for the alcohol content measuring device shown in FIG. 1.

FIG. 3 shows an alternative alcohol content measuring device. Elements corresponding to elements shown in FIG. 1 carry reference numerals increased by 100. Since the semiconductor gas detector 3 of FIG. 1 responds not only to alcohol vapor but also to other reducing gases, FIG. 3 shows a bridge measuring circuit which, in addition to the semiconductor gas detector 103, has a reference detector 103'. Filaments 105 and 105' are connected to the output of pulse generator 109. The second electrodes, 107 and 107', are each connected in one branch of a Wheatstone bridge circuit whose other branches contain resistors 171 and 173. The output of the bridge circuit is applied to the input of a differential amplifier 175. The measurement signal at the output of differential amplifier 175 is applied to linearizing circuit 13. This circuit eliminates errors resulting from reducing gases in the surrounding air.

Figure 4:
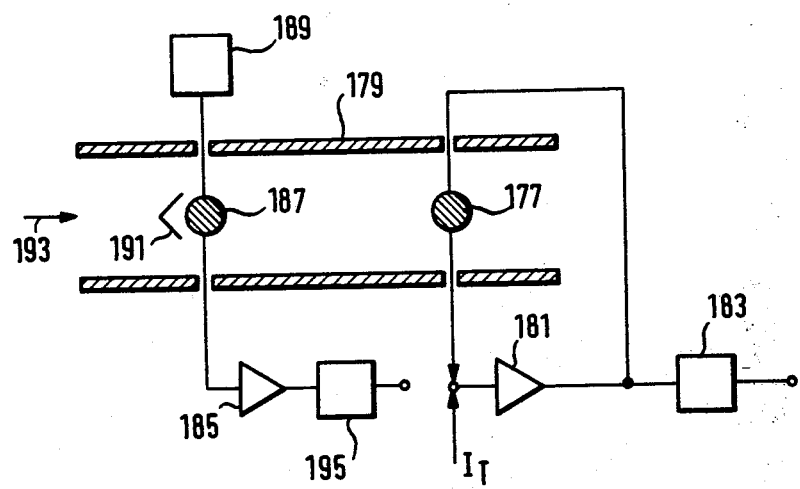
FIG. 4 shows alternate volume measuring and direction sensing devices for the apparatus of FIG. 1.

FIG. 4 shows still another embodiment of the volume measuring and direction sensing devices for the apparatus of FIG. 1. No mechanical moving parts are used in this embodiment. A negative-temperature-coefficient resistor 177 is arranged in channel 193, which corresponds to channel 1 of FIG. 1. Resistor 177 is cooled to a greater or lesser degree depending upon the rate of air flow, causing a corresponding change in its resistance. Resistor 177 is arranged in the feedback circuit of a differential amplifier 181. The gain of differential amplifier 181 therefore varies as a function of the variation of resistance in resistor 177. A signal $I_T$ corresponding to the ambient temperature is applied to the input of differential amplifier 181. The output signal of differential amplifier 181 thus corresponds to the rate of air flow, but is indepeneent of the ambient temperature. This signal is integrated by an integrating circuit 183 at whose output the volume signal is furnished. The error signal is derived from a second negative-temperature-coefficient resistor 187 shielded from the flow of exhaled air by a shield 191, but arranged in the path of inhaled air and thus cooled much more rapidly when the subject inhales than when he exhales. One terminal of resistor 187 is connected to a voltage source 189 and the other to the input of an amplifier 185. The output signal of amplifier 185 is applied to the input of a threshold circuit 195. The threshold circuit 195 is so adjusted that only a large variation in resistance resulting from rapid cooling by inhaled air causes an output signal of the threshold circuit which is the error signal.

Figure 5:
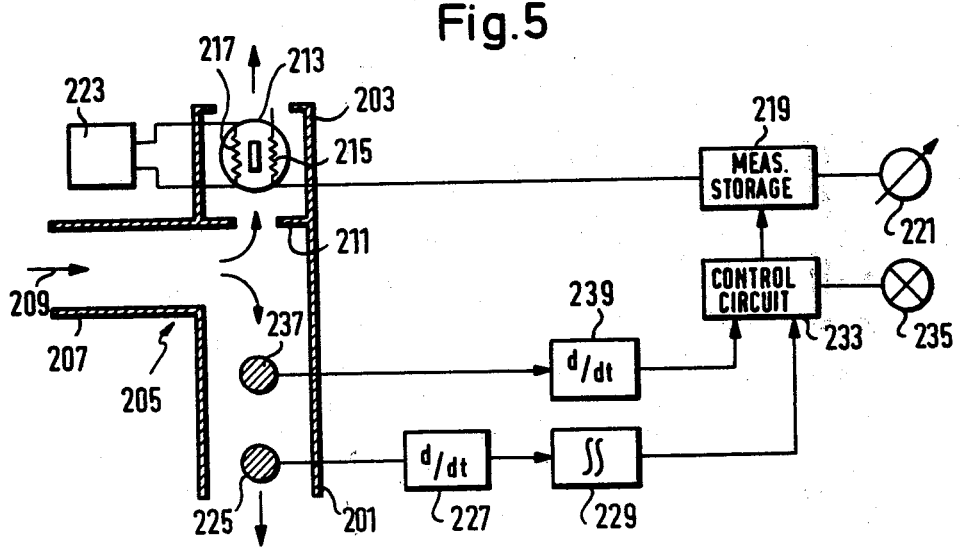
FIG. 5 is a block diagram of a second embodiment of the present invention.

FIG. 5 shows an input channel 205 which is divided into two branches 203 and 201. The subject to be tested breathes into the common portion 207 of the channel in the direction of an arrow 209. Baffles 211 keep the greater portion of the incoming air from channel 203. Most of the exhaled air thus travels from the common portion 207 to branch 201. A semiconductor gas detector 213 is positioned in branch 203. As in the apparatus of FIG. 1, the current through the gas detector is stored in a measurement storage 219 under control of a control circuit 233. An indicator 221 allows the value stored in storage 219 to be read out. The gas detector may be energized by alternating current instead of the pulsed DC of a current source 223.

In this arrangement, the gas detector is not cooled as much by the air exhaled by the subject, thereby eliminating one source of error.

The volume measuring device shown in FIG. 5 includes a rate sensor 225 whose output is applied to a differentiating circuit 227 and thence to a double integrator circuit 229. A second airflow rate sensor 237 furnishes a signal applied to a differentiating circuit 239 whose output is the error signal. As in FIG. 1, the error signal and volume signal are applied to the control circuit 233. A lamp 235 is lit when control circuit 233 furnishes the validity signal. Alternatively, the validity signal may not control the acceptance of the measuring signal by the measurement storage 219 and its indication on indicator 221, but only cause the lighting of light 235.

Sensor 237 is a negative-temperature-coefficient resistor. It is interconnected with the differentiating circuit 239 in such a way that it is warmed by a quiescent current to a temperature between 35° and 38° C. The temperature of resistor 237 thus corresponds approximately to the temperature of air exhaled by the subject. The differentiating circuit 239 thus furnishes an output only for a relatively rapid change in resistance of resistor 237 such as occurs when the subject breathes in cold ambient air. Again, the differentiating circuit also includes a threshold stage which causes minor variations to be suppressed and the error signal to be furnished only when the output of the differentiating circuit exceeds a predetermined minimum amplitude.

Resistor 237 and differentiating circuit 239 may be omitted if sensor 225 is also a negative-temperature-coefficient resistor, and the differentiating circuit 227 also assumes the functions of circuit 239.

Figure 6:
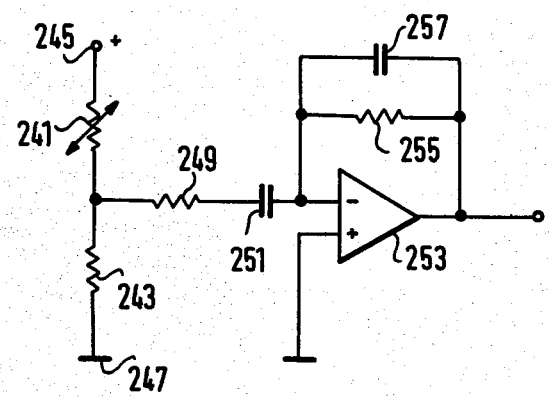
FIG. 6 is a circuit diagram showing a differentiator circuit and a first integrator stage in the volume measuring device of the apparatus of FIG. 5.
Figure 7:
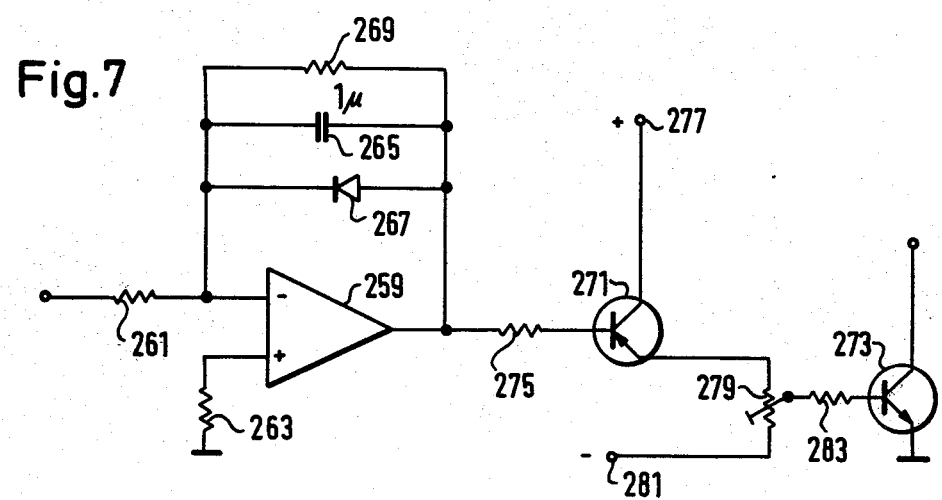
FIG. 7 shows a second integrator circuit of the volume measuring device in FIG. 5.

FIG. 6 shows a portion of the volume measuring circuit from a negative-temperature-coefficient resistor 241 corresponding to resistor 225 to the first stage of the double integrator 229, while FIG. 7 shows the second stage of double integrator circuit 229. A differentiating circuit includes a voltage source having a positive terminal 245 and a ground terminal 247 across which is connected resistor 241 in series with a current limiting resistor 243. The series branch of a resistor 249 and a capacitor 251 is connected between the common point of resistors 241 and 243 and the inverting input of a differential amplifier 253. The signal at the inverting input thus varies as a function of the time rate of change of resistance of resistor 241, any zero drift in said resistor being substantially repressed. The feedback circuit of differential amplifier 253 comprises the parallel combination of resistor 255 and a capacitor 257. Differential amplifier 253 thus acts substantially like a low pass filter or integrator. It is particularly suitable for this purpose since its high input impedance prevents any loading of the differentiating circuit, and its low output impedance is suitable as the input for the next integrating stage which is shown in FIG. 7.

The second integrator stage utilizes a differential amplifier 259 having a feedback resistor 269, a feedback capacitor 265, and a diode 267 connected in parallel. The inverting input of differential amplifier 259 is connected through a resistor 261 to the output of the first integrator stage. Its direct input is connected through a resistor 263 to ground potential. The capacitor 265 must have a relatively large capacitance value since the integration is to be effected over the entire time that the subject breathes out. Resistor 269 must be so chosen that the capacitor 265 can discharge in the interval between measurements, but does not discharge sufficiently during a measurement to affect the result. Use of this resistor allows the elimination of a switch which would otherwise be required to discharge capacitor 265 at the end of the measurement. Diode 267 permits only signals of the same polarity to be integrated.

A threshold stage connected to the output of the second integrator stage comprises a transistor 271 connected as an emitter follower stage from whose variable emitter resistor 279 a signal substantially equal to the integrator output signal is derived. This signal is applied to the base of a transistor 273 whose emitter is connected to ground potential. When the voltage at the base of transistor 273 approaches ground potential, transistor 273 becomes conductive, the voltage at its collector drops. The drop in voltage constitutes the volume signal which indicates that an adequate volume of air has been exhaled by the subject being tested.

The resistance of air flow offered by the negative-temperature-coefficient resistors is relatively low. Condensation of alcohol vapor because of turbulence and pressure differences is therefore unlikely.

Figure 8:
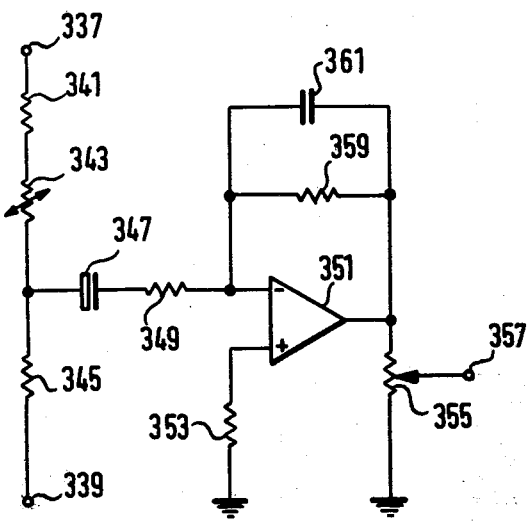
FIG. 8 is a circuit diagram of the direction sensing device in FIG. 5.

FIG. 8 shows a circuit closely similar to that of FIG. 6 and used as a direction sensing device which furnishes an error signal when the subject breathes in. Resistor 343 of FIG. 8 thus corresponds to resistor 237 of FIG. 5. The output of the differentiating circuit is connected to the input of a differential amplifier 351 which functions as a low pass filter having a cutoff frequency at approximately one Hz. This circuit eliminates output signals of the differentiating circuit which arise from somewhat uneven breathing and therefore constitute undesired noise signals.

Figure 9:
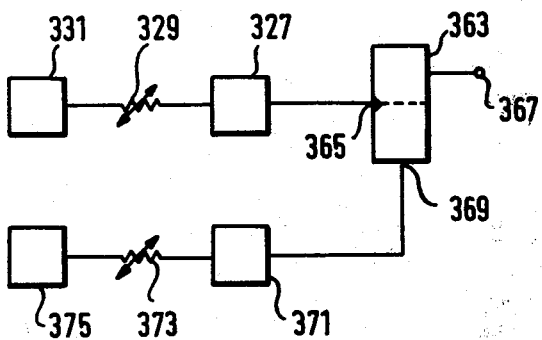
FIG. 9 is a block diagram showing an alternate direction sensing device for the apparatus of FIG. 5.

In describing FIG. 6, it was assumed that the temperature of the surrounding air was lower than that of the exhaled air. If the temperature of the surrounding air rises above approximately 37° C., the polarity of the output signal furnished by a circuit such as that of FIG. 6 reverses. If it is desired that the error signal always have the same polarity, this could be accomplished by connecting an inverter circuit to the output of the circuit of FIG. 6 and connecting this output and the output of the inverter circuit to respective inputs of an OR gate whose output would then be a unidirectional error signal. Further, a circuit like that shown in FIG. 9 could be utilized. In FIG. 9, a dynamic flip-flop 363 is shown. Its state is changed by application of signals to a clock input 365, and it is reset by application of a signal to a reset input 369.

It is desired in this circuit that the signal at the Q output 367 of flip-flop 363 be an unambiguous indication of the direction of air flow. The inhale signal would correspond to the error signal. The flip-flop reacts only to pulses of a given polarity at the clock input. These will be assumed to be positive pulses for purposes of illustration. Connected to clock input 365 is the output of a differentiating circuit 327, whose input is connected to a negative-temperature-coefficient resistor 329 which corresponds to resistor 237 of FIG. 5. The other terminal of resistor 329 is connected to a voltage source 331. The circuit is so arranged that the state of flip-flop 363 may change each time a pulse is received at the output of the differentiating circuit. Thus, a signal may be derived from terminal 367 whose logic level corresponds to the direction of airflow, that is whether the subject is breathing in or breathing out. Since dynamic flipflop 363 should respond only to pulses corresponding to a particular direction of air flow, the switching state of flip-flop 363 is changed by pulses generated by the differentiating circuit when the subject is breathing in counterdirection if the temperature of the surrounding air exceeds the body temperatue. The logic level previously signifying the exhale direction would in this case characterize the inhale direction. That is why a threshold circuit 371 is connected to another input of dynamic flip-flop 363. This causes the state of flip-flop 363 to change as a function of the temperature of the surrounding air. The threshold stage 371 is controlled by a temperature varying resistor 373 which is arranged in the ambient air. The resistor 373 is connected between a voltage source 375 and the threshold stage 371. The threshold of threshold stage 371 is so adjusted that its output level and thereby the switching state of dynamic flip-flop 363 is changed, when the temperature of the surrounding air reaches or exceeds the temperature of the exhaled air.

Figure 10:
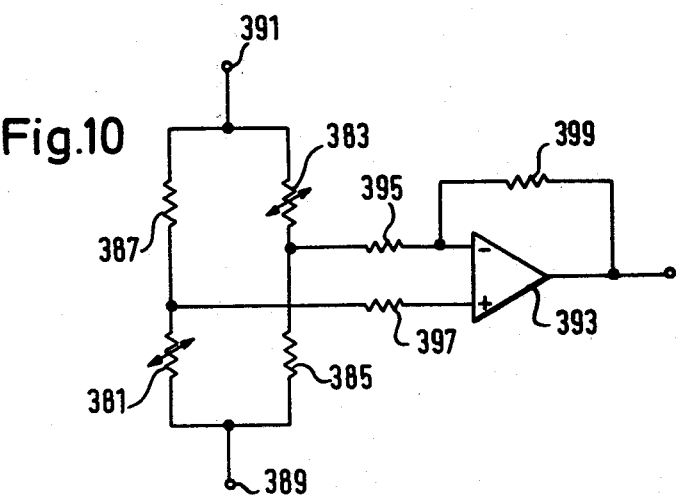
FIG. 10 illustrates a further, alternate, direction sensing device.

An alternate to the circuitry of FIG. 9 is shown in FIG. 10. Here too, two negative-temperature-coefficient resistors, 381 and 383, are provided of which resistor 381 is arranged in the surrounding air while resistor 383 is positioned in the measuring channel. Resistors 381 and 383 are arranged in the opposite arms of a bridge circuit in whose other arms are connected resistors 387 and 385. The bridge is energized by a voltage source having terminals 391 and 389 and the output of the bridge circuit is applied between the inverting and direct inputs of an operational amplifier 393. For feedback purposes, a resistor 399 is connected from the output of amplifier 393 to its inverting input. Because of resistor 381. The polarity of the voltage applied to the input terminals of amplifier 393 changes when the temperature of the surrounding air exceeds the temperature of the exhaled air.

In the preferred embodiments of the present invention, the time constant of the differentiating circuits is approximately 0.5 seconds.

While the invention has been illustrated in several preferred embodiments, it is not to be limited to the circuits and structures shown since many variations thereof will be evident to one skilled in the art and are intended to be encompassed in the present invention as set forth in the following claims.

What is claimed is:

1. Apparatus for measuring the alcohol content in the breath of a subject, comprising, in combination, input means for receiving breath exhaled by said subject; alcohol content measuring means in said input means for measuring said alcohol content and for furnishing a measurement signal indicative thereof; volume measuring means for continually measuring the volume of air exhaled by said subject into said input means furnishing a measured volume signal indicative of the so-measured volume, and furnishing a sufficient volume signal when the total volume of air exhaled by said subject exceeds a predetermined minimum volume; direction sensing means for sensing the direction of air flow in said input means and furnishing an error signal when said direction is indicative of air being inhaled by said subject; and validity signal furnishing means connected to said volume measuring means and said direction sensing means for furnishing a validity signal indicating the validity of said measurement signal only if said volume signal is received prior to said error signal.

2. Apparatus as set forth in claim 1, wherein said volume measuring means comprises rate sensor means in said input means for sensing the rate of air flow therethrough and furnishing a corresponding rate signal, integrator means connected to said rate sensor means for integrating said rate signal and furnishing an integrator output signal corresponding to the so-integrated rate signal, and first threshold means connected to said integrator means for furnishing said sufficient volume signal when said integrator output signal is indicative of a volume exceeding said predetermined minimum volume.

3. Apparatus as set forth in claim 2, wherein said rate sensor means comprises a turbine rotatable in a predetermined direction by air exhaled by said subject, light transmitting means for transmitting light along a predetermined path, photoelectric receiving means for receiving light transmitted by said light transmitting means and furnishing an electric signal in response thereto, and light barrier means coupled to said turbine and rotatable therewith, for alternately blocking and permitting the passage of light from said light transmitting means to said photoelectric receiving means, whereby said photoelectric receiving means furnishes a plurality of electrical signals corresponding in number to the rate of air flow; and wherein said integrator means comprises counting means for counting the number of said electrical signals.

4. Apparatus as set forth in claim 3, wherein said light transmitting and photoelectric receiving means constitute first light transmitting and photoelectric receiving means; and wherein said direction sensing means comprises second light transmitting and photoelectric receiving means offset from said first light transmitting and photoelectric receiving means by a predetermined angle in the direction of rotation of said light barrier means, whereby said first and second photoelectric receiving means alternately furnish electrical signals when the direction of rotation of said light barrier remains unchanged, and said direction sensing means includes error detector circuit means connected to said first and second photoelectric receiving means for furnishing said error signal upon interruption of said alternate furnishing.

5. Apparatus as set forth in claim 2, wherein said direction sensing means comprises a negative temperature coefficient resistance element positioned in said input means, a voltage source connected to said negative temperature coefficient resistance element, means for shielding said negative coefficient resistance element from air exhaled by said subject, whereby the resistance of said negative temperature coefficient resistance element changes only in response to inhaled air, means connected to said negative temperature coefficient resistance element for furnishing an inhale signal in response to said change in resistance, and threshold circuit means connected to said means for furnishing an inhale signal, for furnishing said error signal when the amplitude of said inhale signal exceeds a predetermined amplitude.

6. Apparatus as set forth in claim 4, wherein said negative temperature coefficient resistance element constitutes a first resistance element; wherein said rate sensor means comprises a second negative temperature coefficient resistance element in said input means and exposed to said exhaled air; further comprising a differential amplifier having an input and an output, means for connecting said second negative temperature coefficient element between said output and said input, means for furnishing a temperature signal varying as a function of the ambient temperature in said input means, and means for applying said ambient temperature signal to said input of said differential amplifier, whereby the output of said differential amplifier is substantially independent of the temperature in said input means.

7. Apparatus as set forth in claim 2, further comprising differentiator circuit means connected between said rate sensor means and said integrator means; and wherein said integrator means comprises a first and second integrator circuit connected in cascade.

8. Apparatus as set forth in claim 7, wherein said first and second integrator circuit each comprise an operational amplifier having a capacitor in the feedback path.

9. Apparatus as set forth in claim 8, further comprising a diode connected in parallel with said capacitor in said feedback circuit of said second integrator circuit.

10. Apparatus as set forth in claim 7, wherein said direction sensing means comprises a negative temperature coefficient resistor positioned in said input means, heating means connected to said negative temperature coefficient resistor for heating said negative temperature coefficient resistor to a temperature substantially equal to the temperature of air exhaled from said subject, and differentiating circuit means connected to said negative temperature coefficient resistor for furnishing said error signal in response to a change of resistance of said resistor.

11. Apparatus as set forth in claim 10, further comprising an operational amplifier having an inverting input connected to said differentiating circuit means, an output for furnishing said error signal, and a parallel resistor-capacitor circuit connected from said output to said inverting input.

12. Apparatus as set forth in claim 11, further comprising auxiliary circuit means for furnishing a direction signal indicative of the direction of flow through said input means, independent of the sign of the difference between ambient air temperature and exhaled air temperature.

13. Apparatus as set forth in claim 7, wherein said first or said second integrator circuit comprises a low pass filter.

14. Apparatus as set forth in claim 1, wherein said alcohol content measuring means comprises a semiconductor gas detector having an electrical resistance varying as a function of the alcohol concentration in said input means, a source of electrical energy connected to said semiconductor gas detector for causing a current flow therethrough, and means for measuring the voltage drop across said semiconductor gas detector, the so-measured voltage drop constituting said measurement signal.

15. Apparatus as set forth in claim 14, wherein said semiconductor gas detector includes a first semiconductor gas detector body having a resistance varying also as a function of the concentration of reducing gases other than said alcohol in said input means; and wherein said alcohol content measuring means further comprises a second semiconductor gas detector body positioned outside of said input means, means connecting said first and second gas detector bodies in a bridge circuit furnishing an output signal varying as a function of a difference in resistance between said first and second semiconductor gas detector bodies, and differential amplifier means for receiving said bridge output signal and furnishing said measurement signal in response thereto.

16. Apparatus as set forth in claim 14, further comprising pulse generator means connected to said semiconductor gas detector for furnishing heating pulses thereto.

17. Apparatus as set forth in claim 14, wherein said alcohol content measuring means include means furnishing a reference signal at the start of said measurement; said apparatus further comprising reference storage means for storing said reference signal, measurement storage means for storing said measurement signal, and indicator means connected to said reference storage means and said measurement storage means for furnishing a visual indication corresponding to the difference between the signals stored therein.

18. Apparatus as set forth in claim 14, further comprising linearizing circuit means connected to the output of said semiconductor gas detector.

19. Apparatus as set forth in claim 18, wherein said linearizing circuit means comprises an amplifier having an exponentially varying gain.

20. Apparatus as set forth in claim 5, further comprising temperature regulating means for regulating the temperature in said input means to a constant predetermined temperature.

21. Apparatus as set forth in claim 20, wherein said constant predetermined temperature is approximately 37° C.

* * * * *